(12) United States Patent
Brazeau et al.

(10) Patent No.: US 6,194,384 B1
(45) Date of Patent: *Feb. 27, 2001

(54) LONG-ACTING GALENICAL FORMULATION FOR GRF PEPTIDES

(75) Inventors: Paul Brazeau, Montréal; Denis Gravel, St-Lambert, both of (CA)

(73) Assignee: Theratechnologies, Inc., Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/135,738

(22) Filed: Aug. 18, 1998

Related U.S. Application Data

(63) Continuation-in-part of application No. 08/661,329, filed on Jun. 14, 1996, now Pat. No. 5,817,627.

(51) Int. Cl.[7] ............... A61K 37/02; C07K 7/00
(52) U.S. Cl. ............... 514/12; 514/2; 514/955; 514/960; 530/300; 530/311; 530/324; 424/422; 424/464; 424/468
(58) Field of Search ................... 514/2, 12, 955, 514/960; 530/300, 311, 324; 424/422, 464, 468

(56) References Cited

U.S. PATENT DOCUMENTS

| 4,517,181 | 5/1985 | Ling et al. ............... 514/12 |
| 4,585,756 | 4/1986 | Brazeau, Jr. et al. ............... 514/12 |
| 4,605,643 | 8/1986 | Bohlen et al. ............... 514/12 |
| 4,610,976 | 9/1986 | Bohlen et al. ............... 514/12 |
| 4,626,523 | 12/1986 | Vale et al. ............... 514/12 |
| 4,703,035 | 10/1987 | Rivier et al. ............... 514/12 |
| 4,801,456 | 1/1989 | Drengler et al. ............... 424/422 |
| 5,011,692 | 4/1991 | Fuguoka et al. ............... 424/426 |
| 5,039,660 | 8/1991 | Leonard et al. ............... 514/8 |
| 5,137,669 | 8/1992 | Leonard et al. ............... 264/120 |
| 5,137,872 | 8/1992 | Seely et al. ............... 514/12 |
| 5,137,874 | 8/1992 | Cady et al. ............... 514/17 |
| 5,192,741 | 3/1993 | Orsolini et al. ............... 514/4 |
| 5,817,627 | * 10/1998 | Brazeau et al. ............... 514/12 |

OTHER PUBLICATIONS

Dorland's Illustrated Medical Dictionary, 27 Ed. (WB Saunders Co.) p. 673, 1988.*

* cited by examiner

*Primary Examiner*—Bennett Celsa
(74) *Attorney, Agent, or Firm*—Klauber & Jackson

(57) ABSTRACT

The present invention relates to a long-acting galenical formulation of GRF peptides, GRF and/or analogs thereof which comprises about 1 to about 100 mg of a GRF peptide, fragment or analog thereof pressed from about 1 to about 100 kg/mm$^2$ in a tablet for parenteral administration, whereby these GRF peptides are released as the tablet is eroded.

12 Claims, 5 Drawing Sheets

*=P<0.05, **=P<0.01

LONG-ACTING GALENICAL FORMULATION FOR GRF PEPTIDES

RELATED APPLICATIONS

This application is a continuation-in-part of applications Ser. No. 08/661,329 filed on Jun. 14, 1996 now U.S. Pat. No. 5,817,627 and the content of which is incorporated by reference.

BACKGROUND OF THE INVENTION (a) Field of the Invention

The invention relates to a long-acting galenical formulation of GRF peptides, GRF and/or GRF analogs having a long-lasting and prolonged activity.

(b) Description of Prior Art

Growth hormone (GH) or somatotropin, secreted by the pituitary gland constitute a family of hormones which biological activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulate the growth of the cartilage and the bones (structural growth), the protein synthesis and the cellular proliferation in multiple peripheral organs, including muscles and the skin. Through its biological activity, GH participates within adults at the maintenance of a protein anabolism state, and plays a primary role in the tissue regeneration phenomenon after a trauma.

The decrease of GH secretion with the age, demonstrated in humans and animals, favors a metabolic shift towards catabolism which initiates or participate to the aging of an organism. The loss in muscle mass, the accumulation of adipose tissues, the bone demineralization, the loss of tissue regeneration capacity after an injury, which are observed in elderly, correlate with the decrease in the secretion of GH.

GH is thus a physiological anabolic agent absolutely necessary for the linear growth of children and which controls the protein metabolism in adults.

The secretion of GH by the pituitary gland is principally controlled by two hypothalamic peptides, somatostatin and growth hormone-releasing factor (GRF). Somatostatin inhibits its secretion, whereas GRF stimulates it.

The human GH has been produced by genetic engineering for about ten years. Until recently most of the uses of GH were concerned with growth delay in children and now the uses of GH in adults are studied. The pharmacological uses of GH and GRF may be classified in the following three major categories.

Children Growth

Treatments with recombinant human growth hormone have been shown to stimulate growth in children with pituitary dwarfism, renal insufficiencies, Turner's syndrome and short stature. Recombinant human GH is presently commercialized as an "orphan drug" in Europe and in the United States for children's growth retardation caused by a GH deficiency and for children's renal insufficiencies. The other uses are under clinical trial investigation.

Long Term Treatment for Adults and Elderly Patients

A decrease in GH secretion causes changes in body composition during aging. Preliminary studies of one-year treatment with recombinant human GH reported an increase in the muscle mass and in the thickness of skin, a decrease in fat mass with a slight increase in bone density in a population of aged patients. With respect to osteoporosis, recent studies suggest that recombinant human GH does not increase bone mineralization but it is suggested that it may prevent bone demineralization in post-menopausal women. Further studies are currently underway to demonstrate this theory.

Short Term Treatment in Adults and Elderly Patients

In preclinical and clinical studies, growth hormone has been shown to stimulate protein anabolism and healing in cases of burn, AIDS and cancer, in wound and bone healing.

GH and GRF are also intended for veterinary pharmacological uses. Both GH and GRF stimulate growth in pigs during its fattening period by favoring the deposition of muscle tissues instead of adipose tissues and increase milk production in cows, and this without any undesired side effects which would endanger the health of the animals and without any residue in the meat or milk being produced. The bovine somatotropin (BST) is presently commercialized in the United States.

Most of the clinical studies presently undertaken were conducted with recombinant GH. The GRF is considered as a second generation product destined to replace in the near future the uses of GH in most instances. Accordingly, the use of GRF presents a number of advantages over the use of GH per se.

Physiological Advantages

Growth hormone (GH) is secreted by the pituitary gland in a pulse fashion, since this rhythm of secretion is crucial for an optimal biological activity, the administration of GH to correspond to its natural mode of secretion is difficult to achieve. When GRF is administered in a continuous fashion as a slow releasing preparation or as an infusion, it increases GH secretion while respecting its pulsatility.

The recombinant GH which is presently commercialized is the 22 kDa form whereas GRF induces the synthesis and secretion from the pituitary gland of all the chemical isomers of GH which participate in a wider range of biological activities.

A treatment with GH results in a decreased capacity of the pituitary gland to secrete endogenous growth hormone, and the GH response to GRF is diminished after such a treatment. On the contrary, a treatment with GRF does not present this disadvantages, its trophic action on the pituitary gland increases this gland secreting capacity in normal animals and in patients with somatotroph insufficiency.

Economical Advantages

The production of GH by genetic engineering is very expensive for clinical use. In particular, there are risks of contamination of these commercial preparation with material from the bacterial strain used. These bacterial contaminants may be pyrogens or may result in immunogenic reactions in patients. The purification of the recombinant product is effected by following a plurality of successive chromatography steps. The drastic purity criteria causes multiple quality control steps.

The synthesis of GRF is of chemical nature. The synthesis effected in a solid phase and its purification is carried out in a single step using high performance liquid chromatography (HPLC). Also the quantity of GRF to be administered is much less than the quantity of GH for the same resulting biological activity.

Even with all these advantages, GRF is still not commercialized to date as a therapeutic agent mainly because of its chemical instability. The human GRF is a peptide of 44 amino acids of the following sequence:

```
Tyr Ala Asp Ala Ile Phe Thr Asn Ser Tyr Arg Lys Val Leu Gly Gln    (SEQ ID NO:1)
1             5                   10                  15

Leu Ser Ala Arg Lys Leu Leu Gln Asp Ile Met Ser Arg Gln Gln Gly
            20              25              30

Glu Ser Asn Gln Glu Arg Gly Ala Arg Ala Arg Leu-NH₂.
        35                  40

The minimum active core is hGRF (1-29)NH₂
Tyr Ala Asp Ala Ile Phe Thr Asn Ser Tyr Arg Lys Val Leu Gly Gln    (SEQ ID NO:2)
1             5                   10                  15

Leu Ser Ala Arg Lys Leu Leu Gln Asp Ile Met Ser Arg.
            20              25
```

Clinical studies with children and adults have confirmed that natural hGRF (1-44)NH₂ or the active fragment hGRF (1-29)NH₂ are not potent enough to produce equal effects corresponding to those of recombinant GH.

It is now well documented that hGRF has a very short half-life in serum, being rapidly enzymatically cleaved and inactivated following its injection. As a result, numerous studies have reported that hGRF or its analogs have to be injected daily or several times a day in human and animals to effectively exert its anabolic effect through growth hormone and IGF-I releases. This kind of treatment regimen requiring multiple injections is very time consuming and uncomfortable for the patients, which has so far hampered the clinical use of hGRF and analogs.

Several GRF preparations have been described (U.S. Pat. Nos. 5,137,669, 5,039,660 and 5,192,741, respectively issued on Aug. 11, 1992, Aug. 13, 1991 and Mar. 9, 1993), in which GRF is mixed with various carriers to increase its duration of action. However, all those preparations incorporate carriers that may induce immune or inflammatory reactions following administration.

It would be highly desirable to be provided with a long-acting galenical formulation of GRF peptides, GRF and/or GRF analogs having a long-lasting and prolonged activity without the addition of any carrier.

SUMMARY OF THE INVENTION

One aim of the present invention is to provide a long-acting galenical formulation of GRF peptides, GRF and/or GRF analogs having a long-lasting and prolonged activity without the addition of any carrier.

In accordance with the present invention there is provided a long-acting galenical formulation of GRF peptides, GRF and/or analogs thereof which comprises about 1 to about 100 mg of a GRF peptide, fragment or analog thereof pressed from about 1 to about 100 kg/mm² in a tablet for parenteral administration, whereby these GRF peptides are released as the tablet is eroded by body fluids.

Any GRF peptides, GRF, fragments or analogs thereof may be used in accordance with the present invention. The nature of the GRF peptide is irrelevant to the present invention, as the essence of the present invention resides in the pressed or tablet formulation of any GRF peptides to slow down their erosion and release in body fluids in order to maximize the effect in time. The teachings of U.S. Pat. Nos. 4,517,181, 4,585,756, 4,605,643 and 4,610,976 and U.S. patent applications Ser. No. 08/453,067 filed May 26, 1995; 08/651,645 filed May 22, 1996; 08/702,113 filed Aug. 23, 1996; and 08/702,114 filed Aug. 23, 1996 are all incorporated herein by reference.

The tablet can be pressed from about 1 to about 100 kg/mm², most preferably from about 2 to about 10 kg/mm².

The pressed tablet of the present invention may have a cylindrical shape with a minimal dimension value from about 0.5 mm to about 6 mm. The diameter may be between 0.5 mm to about 6 mm in order to be practically injectable using a needle or trocart for subcutaneous administration to the patient. By using such a gauge 20-16 needle, it avoids having to proceed with a local anesthesia prior to the administration of the tablet. The length of the cylindrical tablet can be between 2 mm to about 40 mm. The tablet can be portioned lengthwise to form a plurality of doses in thinner cylinders (in about 2 to 5 parts).

The diameter and/or the length of the tablet as well as the pressure used in its manufacturing can be varied to adjust the chosen releasing speed of the GRF peptides which is proportional to the desired erosion speed of the tablet for a definite dose.

The dosage to be administered to a patient varies from about 4 to about 40 mg of GRF peptides pressed from about 2 to about 10 kg/mm².

DETAILED DESCRIPTION OF THE INVENTION

Surprisingly and in accordance with the present invention, there is provided a long-acting galenical formulation of a GRF peptide, GRF and analogs thereof which comprises about 4 to about 100 mg of a GRF peptide, fragment or analog thereof pressed from about 1 to about 100 kg/mm² in a tablet for parenteral administration, whereby the GRF peptide is released as the tablet is eroded in a selected time schedule.

The tablet of the present invention can release GRF peptide for up to at least 14 days.

In accordance with a preferred embodiment of the present invention, there is provided a long-acting galenical formulation comprising about 1 to about 100 mg of a GRF peptide, a derivative thereof or an analog thereof having the activity of that of GRF of the formula (I):

$$Ra-X \tag{I}$$

wherein Ra is:

a hydrogen, cis or trans CH$_3$—CH$_2$—CH=CH—CH$_2$—CO—, or one element selected from a cis or a trans enantiomer or a racemic mixture of:

(1)
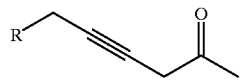

(2)

(3)

(4)

(5)

(6)

(7)
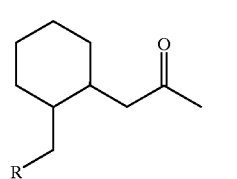

(8)
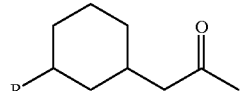

(9)
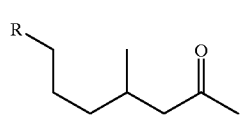

(10)
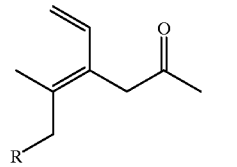

(11)
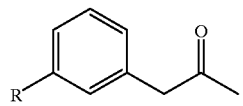

(12)
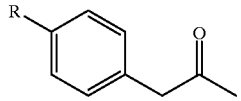

(13)
CH$_3$CH$_2$—C≡C—CH$_2$—CO

(14)
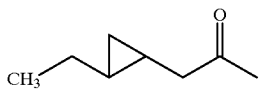

(15)
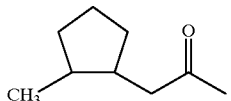

(16)
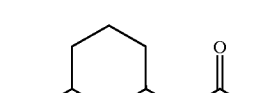

and

(17)
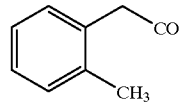

wherein R is a hydrogen or a lower alkyl; and

X is a GRF peptide selected from the group consisting of SEQ ID NO:1 and SEQ ID NO:2 wherein said GRF peptide, derivative thereof or analog thereof is pressed from about 1 to about 100 kg/mm$^2$ in a tablet for parenteral administration, whereby said GRF peptide, derivative thereof or analog thereof is released as the tablet is eroded.

The term lower alkyl is intented to include methyl or ethyl.

Preferably X in the long-acting galenical formulation described above is as set forth in SEQ ID NO:2.

Figure 1A:
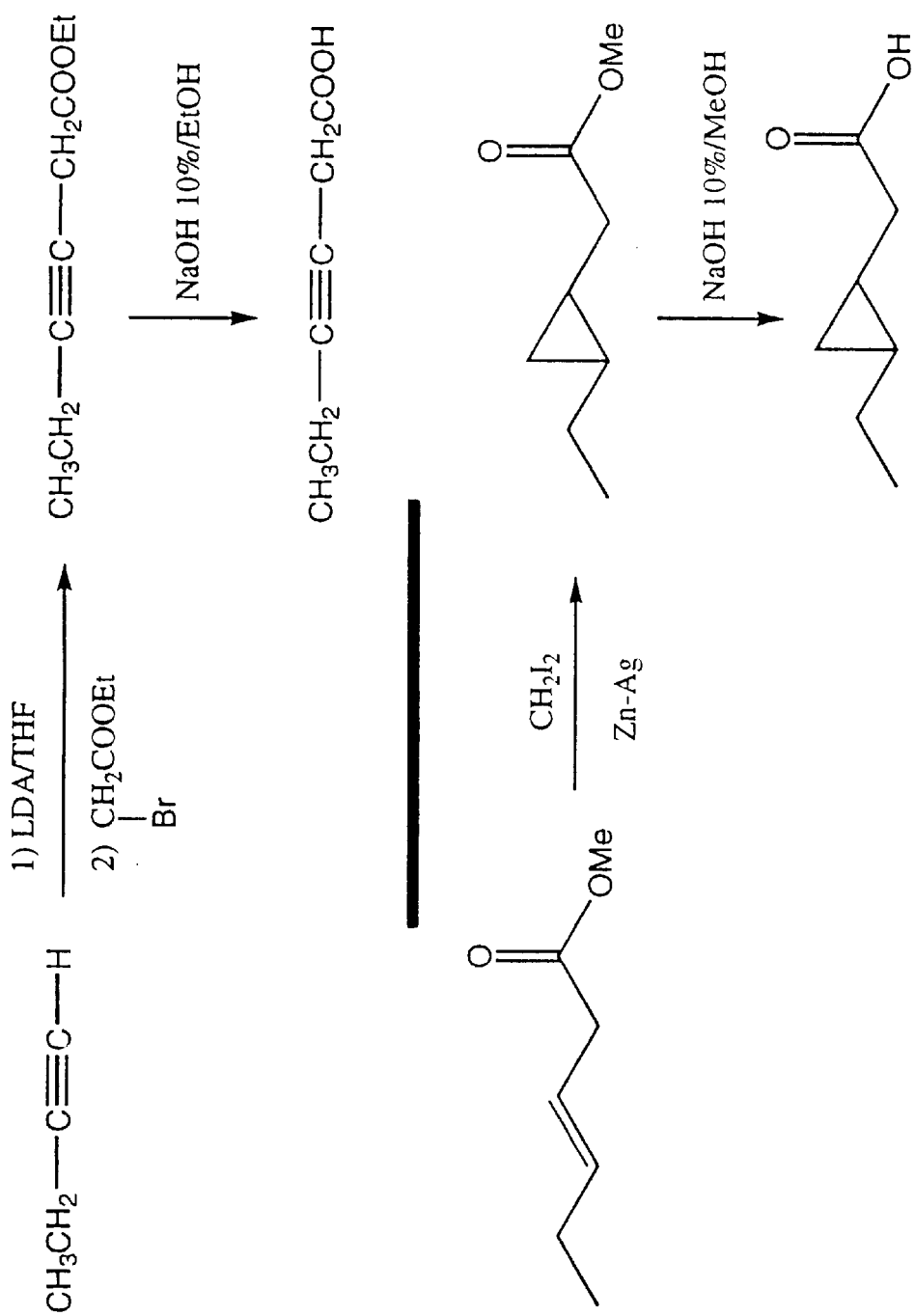
FIGS. 1A to 1C illustrate examples of specific synthesis of preferred radicals R in accordance with the present invention.
Figure 1B:
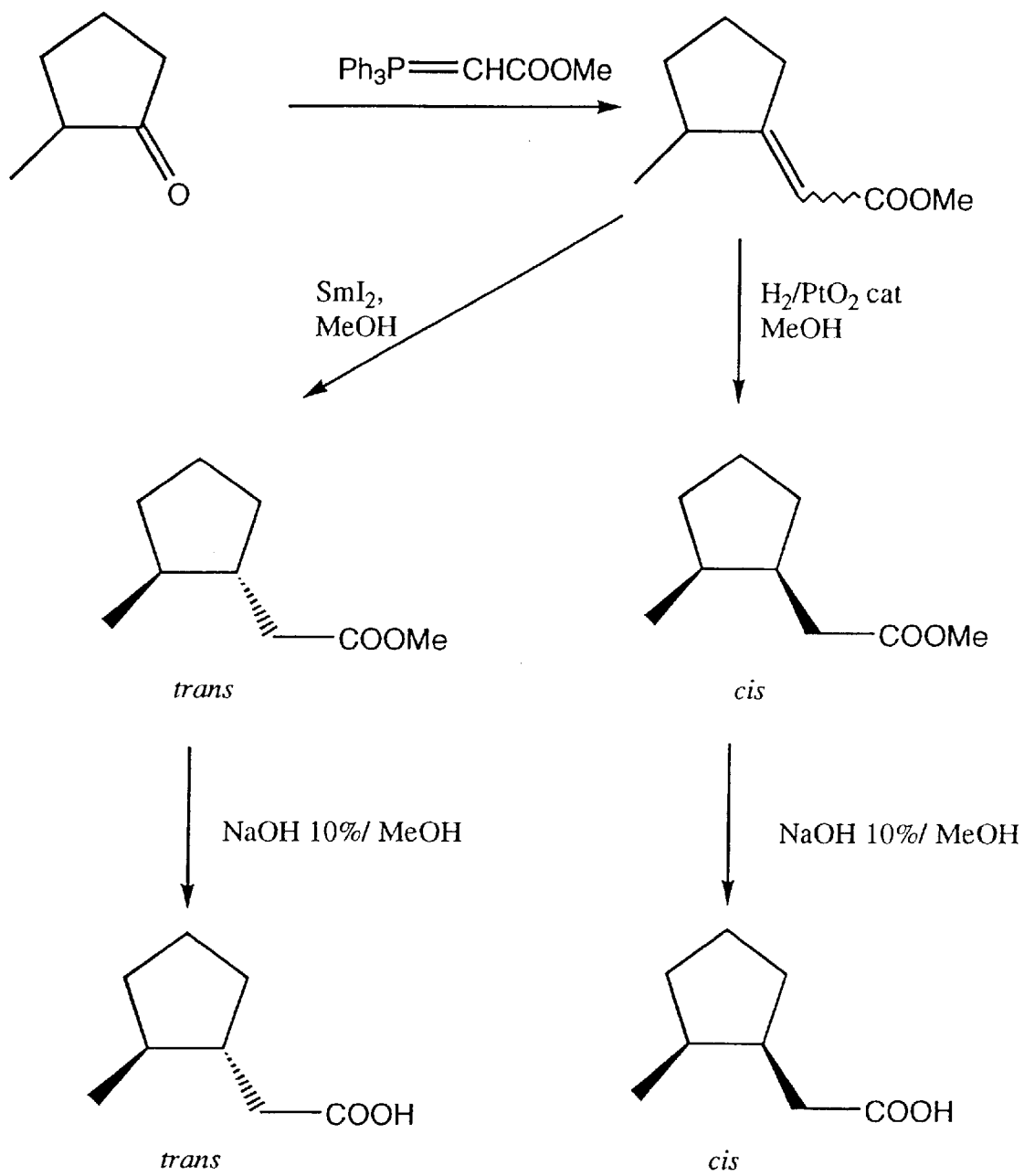
Figure 1C:
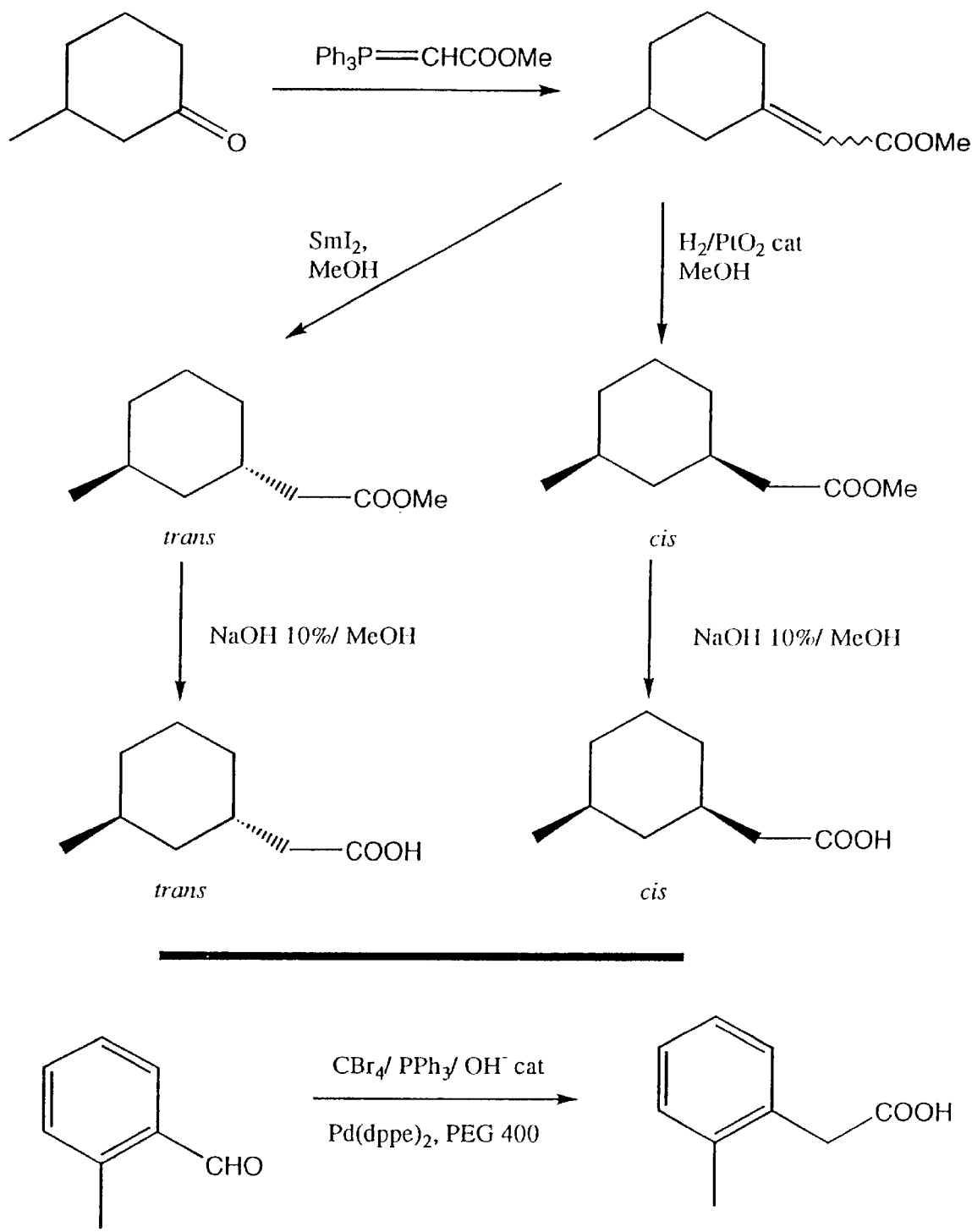

FIGS. 1A to 1C illustrate examples of specific synthesis of preferred radical R listed above in accordance with the present invention.

The preferred tablet of the present invention is pressed at about 6.5 kg/mm$^2$.

In accordance with the present invention, pig was selected as a test species, since it is a valuable preclinical model for the testing of the GRF formulation tablet of the present invention. Indeed, human and porcine GRF(1-29)NH$_2$ share a 100% homology of structure, and the physiological pattern of GH secretion is almost identical in both species.

Moreover, the potency of the long-acting galenical GRF formulation was assessed as its ability to significantly increase IGF-I blood levels rather than its acute GH releasing potency. Indeed, it is known that the anabolic and healing effects of GH or GRF induced GH are mediated by an increase in IGF-I synthesis and secretion, a more easy and thorough indication of all anabolic effect of an improved GH secretion. Therefore, the measurement of GRF induced IGF-I elevation is the best indicator of the treatment efficacy.

The present invention will be more readily understood by referring to the following examples which are given to illustrate the invention rather than to limit its scope.

EXAMPLE I

Effect of a Tablet Made of Mechanically Compressed (Hexenoyl trans-3)$_0$ hGRF (1-29) NH$_2$ on IGF-I Secretion in Pigs This experiment was conducted to assess the potency of a long-acting GRF preparation, made of compressed (Hexenoyl trans-3)$_0$ hGRF (1-29) NH$_2$, without the addition of any other excipient.

(Hexenoyl trans-3)$_0$ hGRF (1-29) NH$_2$ is a combination of the natural hGRF(1-29)NH$_2$ and a natural fatty acid, which has already been described in co-pending U.S. patent application Ser. No. 08/453,067 filed on May 26, 1995, the content of which is incorporated herein by reference.

Identity of Test Articles

|   |   |
|---|---|
|   | Control |
| A | (Hexenoyl trans-3)$_0$ hGRF (1–29) NH$_2$, compression A, 14 mg at 6.5 kg/mm$^2$ |
| B | (Hexenoyl trans-3)$_0$ hGRF (1–29) NH$_2$, compression B, 14 mg at 16.5 kg/mm$^2$ |

Both (Hexenoyl trans-3)$_0$ hGRF (1-29) NH$_2$ treatments differ by the fact that the tablets are made with a different level of mechanical compression (6.4 vs. 16.0 kg/mm$^2$).

Route and Frequency of Test Article Administration

Subcutaneous injection of the tablets.

Test System

Landrace x Yorkshire pigs.

Animal Description

Twenty-four (24) growing barrows pigs weighing 35 kg at the time of purchase.

Ration

Commercial feed concentrate (18% minimum) protein offered ad libitum.

Experimental design

Twenty-four (24) pigs will be randomly distributed into 3 experimental groups (n=8 pigs/group).

|   |   |
|---|---|
| Group 1 | Control |
| Group 2 | (Hexenoyl trans-3)$_0$ hGRF (1–29) NH$_2$, 14 mg, compressed tablet A |
| Group 3 | (Hexenoyl trans-3)$_0$ hGRF (1–29) NH$_2$, 14 mg, compressed tablet B |

The tablets were surgically subcutaneously inserted following pig light anesthesia.

Blood samples for IGF-I measurement were collected daily, from 2 days before to 14 days after tablets implantation and finally at 40 days post-implantation. Blood samples were allowed to clot at +40° C. Serum were harvested by centrifugation, stored at −20° C. and assayed for IGF-I.

Figure 2:
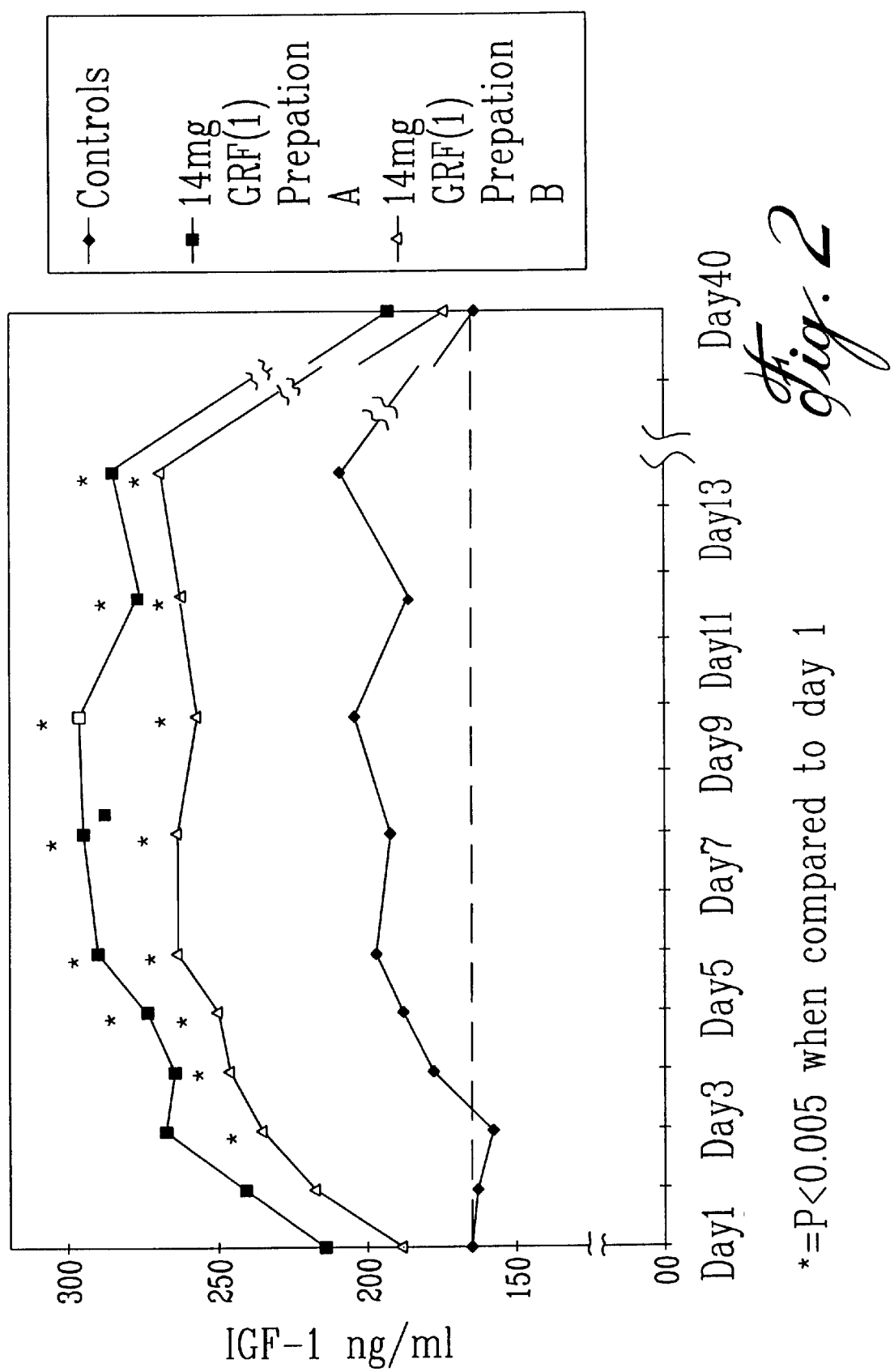
FIG. 2 illustrates the effect of a tablet made of mechanically compressed (Hexenoyl trans-3)₀ hGRF (1-29) NH₂ on IGF-I secretion in pigs.

The results shown in FIG. 2 demonstrate that IGF-I levels did not vary significantly over the study period in the control group. In contrast, it is increased over basal values (day 1: pre-implantation), this increase being statistically significant from day 3 to day 14 following implantation of the GRF tablets. The IGF-I increase ranged from 24% to 42% in the group injected with preparation A (14 mg GRF; 6.4 kg/mm$^2$) and from 25% to 43% in the group injected with preparation B (14 mg GRF; 16.0 kg/mm$^2$) between day 3 and 16 over day 1. No difference was observed between both GRF-treated groups, indicating that both compression intensities tested (6.4 vs. 16.0 kg/mm$^2$) were equally effective in providing a slow releasing formulation for GRF.

Finally, on day 40 following implantation, IGF-I levels were returned to pre-implantation levels in both GRF groups.

EXAMPLE II

Effect of a Tablet Made of Mechanically Compressed (Hexenoyl trans-3)$_0$ hGRF (1-44) NH$_2$ on IGF-I Secretion in Pigs This experiment is conducted to assess the potency of a long-acting GRF preparation, made of compressed (Hexenoyl trans-3)$_0$ hGRF (1-44) NH$_2$, without the addition of any other excipient.

(Hexenoyl trans-3)$_0$ hGRF (1-44) NH$_2$ is a combination of the natural hGRF(1-44)NH$_2$ and a natural fatty acid, which has already been described in co-pending U.S. patent application Ser. No. 08/453,067 filed on May 26, 1995 and the content of which is hereby incorporated by reference.

Identity of Test Articles

|   |   |
|---|---|
|   | Control |
| A | (Hexenoyl trans-3)$_0$ hGRF (1–44) NH$_2$, compression A, 14 mg at 6.5 kg/mm$^2$ |
| B | (Hexenoyl trans-3)$_0$ hGRF (1–44) NH$_2$, compression B, 14 mg at 16.5 kg/mm$^2$ |

Both (Hexenoyl trans-3)$_0$ hGRF (1-44) NH$_2$ treatments differ by the fact that the tablets are made with a different level of mechanical compression (6.4 vs. 16.0 kg/mm$^2$).

Route and Frequency of Test Article Administration

Subcutaneous injection of the tablets.

Test System

Landrace x Yorkshire pigs.

Animal Description

Twenty-four (24) growing barrows pigs weighing 35 kg at the time of purchase.

Ration

Commercial feed concentrate (18% minimum) protein offered ad libitum.

Experimental Design

Twenty-four (24) pigs are randomly distributed into 3 experimental groups (n=8 pigs/group).

|   |   |
|---|---|
| Group 1 | Control |
| Group 2 | hGRF (1–44) NH$_2$, 30 mg/3 ml H$_2$O |
| Group 3 | hGRF (1–44) NH$_2$, 14 mg (2 × 7.5 mg), compressed tablet A |
| Group 4 | (Hexenoyl trans-3)$_0$ hGRF (1–44) NH$_2$, 14 mg (2 × 7.5 mg), compressed tablet B |

The tablets are surgically subcutaneously inserted following pig light anesthesia.

Blood samples for IGF-I measurement are collected daily, from 2 days before to 14 days after tablets implantation and finally at 40 days post-implantation. Blood samples are allowed to clot at +4° C. Serum are harvested by centrifugation, stored at −20° C. and assayed for IGF-I.

Figure 3:
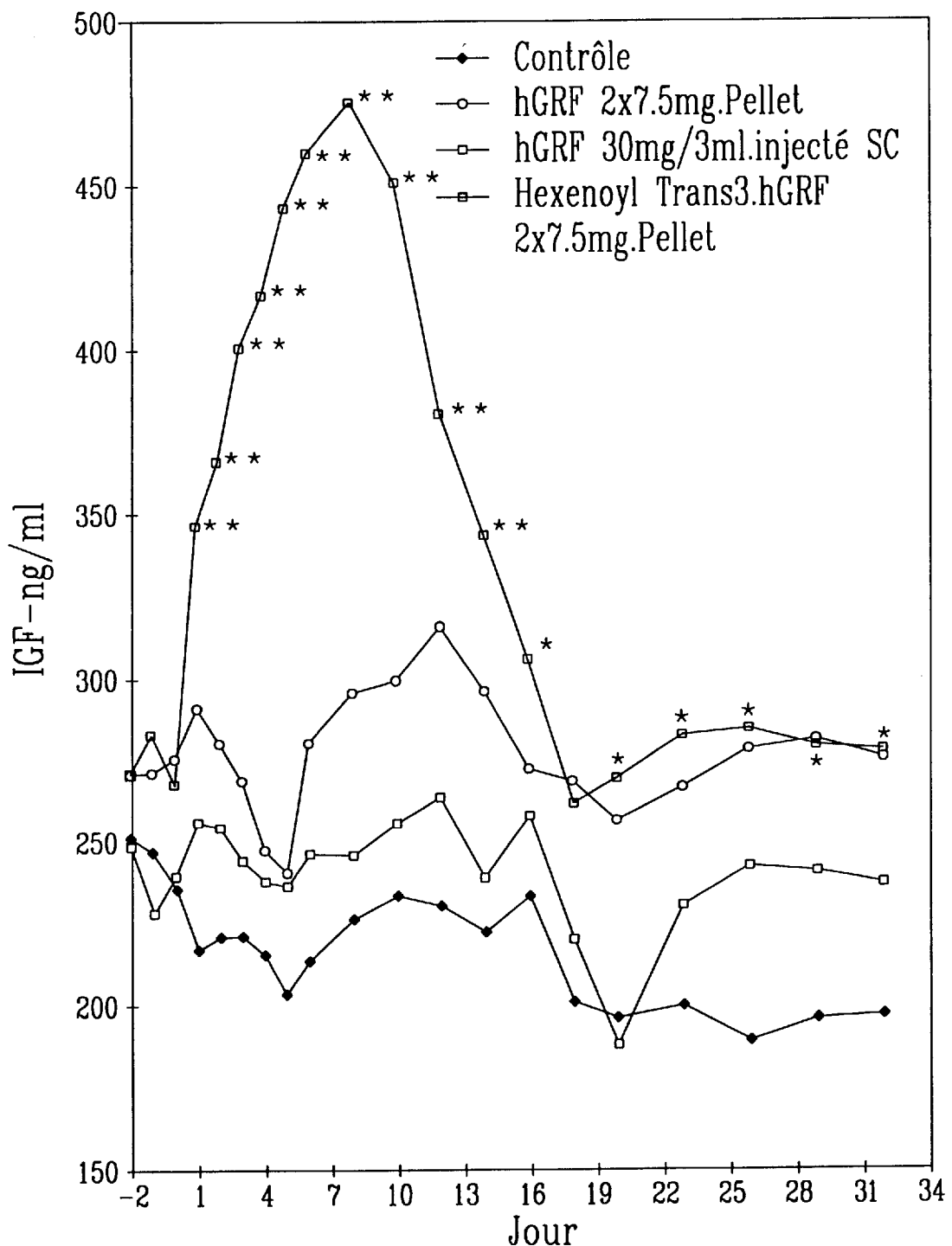
FIG. 3 illustrates the effect of a tablet made of mechanically compressed (Hexenoyl trans-3)₀ hGRF (1-44) NH₂ on IGF-I secretion in pigs.

FIG. 3 illustrates the effect of a tablet made of mechanically compressed (Hexenoyl trans-3)$_0$ hGRF(1-44) NH$_2$ on IGF-I secretion in pigs. The results demonstrate that IGF-I levels do not vary significantly over the study period in the control group. In contrast, it is increased over basal values following implantation of the GRF tablets.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

---

We claim:

1. A long-acting galenical formulation comprising about 1 to about 100 mg of a GRF compound having the activity of that of GRF, wherein said GRF compound is of the formula (I):

Ra—X                                  (I)

wherein Ra is:

one element selected from a cis or a trans enantiomer or a racemic mixture of:

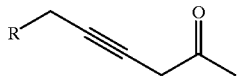

(1)

(2)

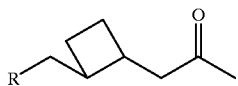
(3)

(4)

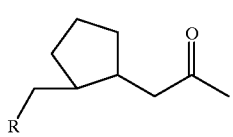
(5)

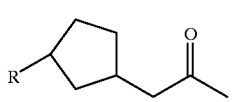
(6)

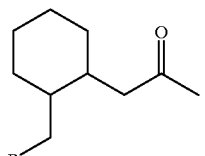
(7)

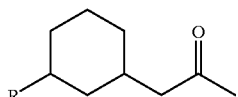
(8)

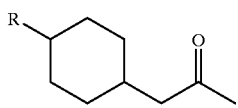
(9)

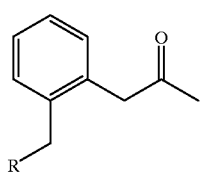
(10)

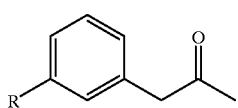
(11)

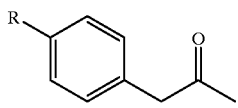
(12)

(13)

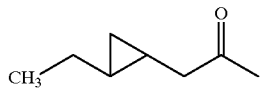
(14)

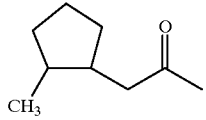
(15)

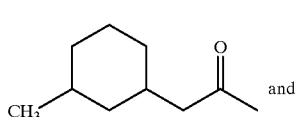
and (16)

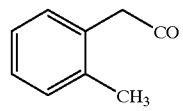
(17)

wherein R is a hydrogen or a lower alkyl; and

X is a GRF peptide selected from the group consisting of SEQ ID NO:1 and SEQ ID NO:2, wherein said GRF compound is pressed from about 1 to about 100 kg/mm$^2$ in a tablet for parenteral administration, whereby said GRF compound is released as the tablet is eroded.

2. The galenical formulation of claim 1, wherein the tablet is pressed from about 2 to about 10 kg/mm$^2$.

3. The galenical formulation of claim 1, wherein the tablet has a cylindrical shape with a diameter between 0.5 mm to about 6 mm and a length between 2 mm to about 40 mm.

4. The galenical formulation of claim 1 having a dosage of about 4 to about 40 mg of GRF peptides.

5. The galenical formulation of claim 1, wherein said lower alkyl is a methyl or an ethyl.

6. The galenical formulation of claim 5, wherein the tablet is pressed from about 2 to about 10 kg/mm$^2$.

7. The galenical formulation of claim 5, wherein the tablet has a cylindrical shape with a diameter between 0.5 mm to about 6 mm and a length between 2 mm to about 40 mm.

8. The formulation of claim 5 having a dosage of about 4 to about 40 mg of said GRF compound.

9. The galenical formulation of claim 1, wherein X is as set forth in SEQ ID NO:2.

10. The galenical formulation of claim 9, wherein the tablet is pressed from about 2 to about 10 kg/mm$^2$.

11. The galenical formulation of claim 9, wherein the tablet has a cylindrical shape with a diameter between 0.5 mm to about 6 mm and a length between 2 mm to about 40 mm.

12. The formulation of claim 9 having a dosage of about 4 to about 40 mg of said GRF compound.

* * * * *

UNITED STATES PATENT AND TRADEMARK OFFICE
CERTIFICATE OF CORRECTION

PATENT NO. : 6,194,384 B1
DATED : February 27, 2001
INVENTOR(S) : Paul Brazeau, et al.

It is certified that error appears in the above-identified patent and that said Letters Patent is hereby corrected as shown below:

Column 7,
Line 53, please correct the expression "+40°C" with the expression "+4°C."

In the legend,
Fig. 2, please substitute the term "preparation" for the term "prepation", in two instances.
Fig. 3, please substitute the legend of Fig. 3 for the following legend:
—♦— Control
—O— hGRF 2X7.5mg.Pellet
—□— hGRF 30mg/3ml.injected SC
—⊞— Hexenoyl Trans3.hGRF 2X7.5mg.Pellet Column 5,
Between the structure structure:

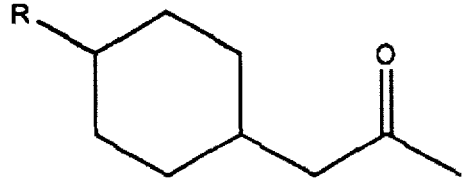

lines 50 and 55, please correct of Formula (9) for the following

Lines 55 to 60, Formula 10 as

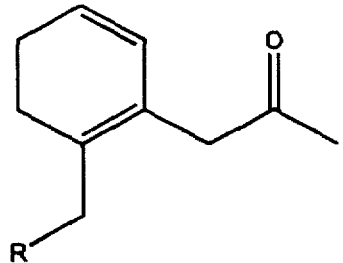

please correct the structure of follows:

UNITED STATES PATENT AND TRADEMARK OFFICE
CERTIFICATE OF CORRECTION

PATENT NO.    : 6,194,384 B1
DATED         : February 27, 2001
INVENTOR(S)   : Paul Brazeau, et al.

It is certified that error appears in the above-identified patent and that said Letters Patent is hereby corrected as shown below:

<u>Column 8,</u>
Lines 45 to 52, please substitute the table containd therein for the following table.

| | |
|---|---|
| Group 1 | Control |
| Group 3 | hGRF (1-44) $NH_2$, 30 mg/3 ml $H_2O$ |
| Group 2 | hGRF (1-44) $NH_2$,, (2 x 7.5 mg), Compressed table A |
| Group 4 | (Hexenoyl trans-3)$_o$ hGRF (1-44) $NH_2$, 14 mg (2 x 7.5 mg), compressed tablet B |

Signed and Sealed this

Sixteenth Day of October, 2001

*Attest:*

NICHOLAS P. GODICI
*Attesting Officer*     *Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 44 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:1:

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```

(2) INFORMATION FOR SEQ ID NO:2:

(i) SEQUENCE CHARACTERISTICS:
      (A) LENGTH: 29 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:2:

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```